United States Patent [19]
Amjad

[11] Patent Number: 4,892,724
[45] Date of Patent: * Jan. 9, 1990

[54] TARTAR INHIBITING ORAL COMPOSITIONS AND METHOD

[75] Inventor: Zahid Amjad, Avon Lake, Ohio

[73] Assignee: The B. F. Goodrich Company, Akron, Ohio

[*] Notice: The portion of the term of this patent subsequent to Jan. 9, 2007 has been disclaimed.

[21] Appl. No.: 191,668

[22] Filed: May 9, 1988

[51] Int. Cl.$^4$ .................. A61K 7/16; A61K 7/18; A61K 9/68

[52] U.S. Cl. ............................ 424/49; 424/52

[58] Field of Search .................... 424/49, 52

[56] References Cited

U.S. PATENT DOCUMENTS 3,937,807  2/1976  Haefele .................... 424/52
3,959,458  5/1976  Agricola et al. .............. 424/52
4,627,977  12/1985  Gaffar et al. ................ 424/52

Primary Examiner—John Kight
Assistant Examiner—Nathan M. Nutter
Attorney, Agent, or Firm—George A. Kap; Nestor W. Shust

[57] ABSTRACT

Oral compositions and a method for inhibiting tartar on teeth are disclosed herein, said compositions are characterized by the presence of a fluoride source, a dental abrasive, and an anticalculus agent which is an admixture of at least one phosphorus-containing compound and at least one polymer selected from homopolymers of a carboxylic monomer and copolymers containing at least 30% of said carboxylic monomer and at least 5% by weight of a comonomer. The phosphor-containing compound is preferably selected from phosphonic acids and phosphonoalkane carboxylic acids.

19 Claims, No Drawings

TARTAR INHIBITING ORAL COMPOSITIONS AND METHOD

BACKGROUND OF THE INVENTION

This invention relates to oral compositions containing an anticalculus agent which is a combination of a phosphorus-containing compound and a polymer selected from homopolymers of a carboxylic monomer and copolymers thereof containing at least 30% of said carboxylic monomer. This invention also relates to a method for inhibiting dental calculus on teeth.

Tartar or dental calculus is calcified plaque and plaque is the culprit of gum disease. Tartar is a deposit which forms on the surfaces of the teeth at the gingival margin. Mature calculus consists of an inorganic portion which is largely calcium phosphate arranged in a hydroxyapatite crystal lattice structure similar to bone, enamel and dentine. An organic portion is also present and consists of salivary sediment, food debris, and various types of microorganisms.

It is generally agreed that calcium and orthophosphate form the crystalline material known as hydroxyapatite which is dental calculus, i.e., a mineralized, hard formation which forms on teeth. The precursor to crystalline hydroxyapatite is amorphous calcium phosphate which differs from hydroxyapatite in atomic structure, crystal morphology, and stoichiometry. The x-ray diffraction pattern of amorphous calcium phosphate shows broad peaks typical of amorphous materials which lack the long range atomic order characteristic of all crystalline materials, including hydroxyapatite.

It is generally well known that linear molecularly dehydrated polyphosphates, such as hexametaphosphate, tripolyphosphate, pyrophosphate, and the like, are effective calcium and magnesium ion suppressors, inhibitors, sequestrants and/or chelating agents. Such materials are also known to be effective inhibitors of hydroxyapatite formation in vitro. It is also known that such polyphosphates, when introduced into the oral cavity and/or saliva, are significantly hydrolyzed by salivary enzymes, i.e., polyphosphates to orthophosphates which are ineffective as inhibitors of hydroxyapatite formation.

Studies have shown that there is a good correlation between the ability of a compound to prevent hydroxyapatite crystalline growth in vitro and its ability to prevent calcification in vivo, provided that such compound is stable in and inert to saliva and its components.

REFERENCE TO RELATED APPLICATION

A related application was filed for inventor Amjad on Dec. 21, 1987, entitled "Dental Calculus Inhibiting Compositions" and bearing Ser. No. 135,803, and now U.S. Pat. No. 4,841,847. The anticalculus agents disclosed in that application are same as herein but devoid of phosphorus-containing compound.

SUMMARY OF THE INVENTION

Oral compositions are characterized by the presence of a fluoride source, dental abrasive, and an anticalculus agent which is stable in the presence of saliva or salivary enzymes. The anticalculus agent is a combination or a mixture of a phosphorus-containing compound and a carboxylic polymer selected from homopolymers of monounsaturated monocarboxylic and dicarboxylic acids of 3 to 5 carbon atoms, and from copolymers containing at least 30% by weight of such acids, and at least 5% by weight of a principal comonomer. This invention is also directed to a method for inhibiting tartar formation by applying to the teeth one of the oral compositions disclosed herein. The anticalculus agents herein produce synergistic results and are effective in absence of germicidal compositions.

DETAILED DESCRIPTION OF THE INVENTION

The oral compositions disclosed and claimed herein are characterized by the presence of a fluoride source, a dental abrasive or a polishing agent, a vehicle, and an anticalculus agent selected from a combination or a mixture of a phosphorus-containing compound and a carboxylic polymer selected from homopolymers of monounsaturated monocarboxylic and dicarboxylic acids of 3 to 5 carbon atoms and from copolymers containing at least 30% by weight of a monounsaturated monocarboxylic or a dicarboxylic acid of 3 to 5 carbons, its anhydride, or a water-soluble salt of such acid. The phosphorus-containing compound is selected from amino phosphonic acids and phosphonates, diphosphonic acids, phosphonoalkanecarboxylic acids, hydroxy phosphonocarboxylic acids, polyphosphoric acids, and polyol phosphate esters.

Comonomers which can be copolymerized with one or more of the acids or salts thereof include acrylamides, alkyl acrylates, alkyl itaconates, vinyl sulfonic acid, hydroxyalkyl acrylates, alkoxyalkyl acrylates, lower alkenyl carboxylates, styrene sulfonic acids, allyloxyhydroxyalkane sulfonic acids, acrylamidoalkane sulfonic acids, sulfoloweralkyl acrylates, polymerized vinyl alcohols, anhydrides and salts thereof. Such anticalculus agents can be used in conjunction with other additives, including other anticalculus agents.

This invention is also directed to a method for inhibiting dental calculus by applying to the teeth a calculus-inhibiting amount of the oral composition described and claimed herein.

A fluoride source, a dental abrasive and vehicle selected from water or water plus a humectant, as well as an anticalculus agent, are essential ingredients of the oral compositions of this invention. Amount of the anticalculus or tartar control agent in the oral compositions claimed herein is about 0.01 to 10% by weight, preferably 0.1 to 5%. Weight ratio of the phosphorus-containing compound to the polymer is in the range of 1:10 to 10:1, preferably 1:5 to 5:1, and especially 1:4 to 1:1.

The phosphorus-containing compound is selected from amino phosphonic acids and phosphonates, diphosphonic acids, phosphonoalkane carboxylic acids, hydroxy phosphonocarboxylic acids, polyphosphoric acids, polyol phosphate esters, and mixtures thereof.

Certain organophosphorus compounds, such as aminomethylene phosphonic acid, N-substituted aminomethylene phosphonic acids, and both N- and C-substituted aminomethylene phosphonic acids, are suitable herein. These compounds can be prepared pursuant to the disclosure of U.S. Pat. No. 3,288,846. Generally, such compounds can be characterized as containing at least one N-C-P linkage in their molecules, and have the following structural formula:

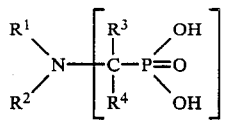

wherein $R^3$ and $R^4$ are individually selected from hydrogen and organic radicals, preferably hydrogen; $R^1$ and $R^2$ are individually selected from hydrogen, organic radicals, and alkylene phosphonic radicals, such as are within the brackets, above. Salts of the above compounds can also be used. Examples of this group of compounds include aminotri (methylene phosphonic acid) and the potassium salt of hexamethylenediamine tetra (methylene phosphonic acid).

Certain hydroxyalkane -1, 1- diphosphonic acids described in U.S. Pat. No. Re 28,553 are useful herein. Preferred compounds in this group are defined by the following structural formula:

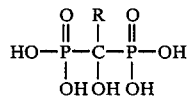

wherein R is a lower alkyl radical of 1 to 5 carbon atoms. The OH groups can be in esterified form and two or more molecules can be converted to corresponding anhydrides. An especially useful compound in this group is 1 - hydroxyethylethane -1, 1- diphosphonic acid, also referred to as HEDP.

Certain of the phosphono acids disclosed in U.S. Pat. No. 3,886,205 can be used as the phosphorus-containing compounds. These compounds are generally defined as follows:

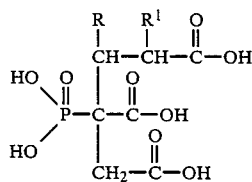

wherein R can be hydrogen, lower alkyl of 1 to 5 carbons or carboxyl and $R^1$ can be hydrogen or methyl. Alkali metal, ammonium or amine salts of the above compounds are also suitable. These compounds are also referred to herein as phosphonoalkane di-and tricarboxylic acids containing 2 to 6 carbon atoms in the alkane group. An especially effective compound in this group is 2 - phosphonobutane -1, 2, 4 - tricarboxylic acid.

Another phosphorus-containing compound useful herein is the hydroxyphosphonocarboxylic acid having the following formula:

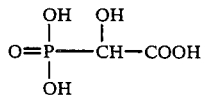

This acid, and its salts, is a phosphonoalkane carboxylic acid, more specifically a phosphonoalkane monocarboxylic acid.

Useful phosphorus-containing compounds are also disclosed by U.S. Pat. No. 2,358,222. This group of polyphosphoric acid compounds include pyrophosphates, metaphosphates and complex phosphates. The polyphosphates, such as pyrophosphates, triphosphate, tetraphosphate, hexametaphosphate, and complex phosphate, are generally derived by molecular dehydration of orthophosphoric acid compounds.

The polyolphosphate esters contain one or more 2-hydroxyethyl groups and one or more of the following groups:

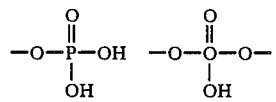

and salts thereof. Preparation of such compounds is disclosed in U.S. Pat. No. 3,462,365, of which, glycerine phosphate esters are preferred. Also included in this group of compounds are the phosphated mixed esters of non-surface active polyols containing at least one hydroxyethyl group and monohydric surface active compounds containing oxyethylene groups, described in U.S. Pat. No. 3,723,420.

The amino phosphonates useful as phosphorus-containing compounds are defined as follows:

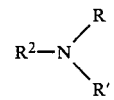

where R is

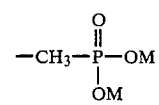

and
$R^1$ is R or $-CH_2CH_2OH$ and $R^2$ is R, $-CH_2CH_2OH$ or

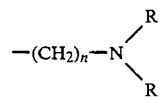

where M is hydrogen, ammonium, alkali metal, or a combination thereof, and n is 1 to 6. Such compounds are described in U.S. Pat. No. 3,336,221. Other useful amino phosphonates are described in U.S. Pat. No. 3,434,969.

Particularly preferred phosphorus-containing compound is selected from compounds which contain the phosphono group

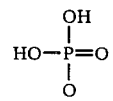

and especially amino phosphonic acids, diphosphonic acids, phosphonoalkane carboxylic acids, and mixtures thereof. Specific examples of such phosphorus-containing compounds include aminotri(methylene phosphonic acid), hydroxyethane, 1,1-diphosphonic acid, and 2-phosphonobutane-1,2,4-tricarboxylic acid.

The homopolymers of the carboxylic acids, anhydrides and salts thereof, and the copolymers have molecular weight in the range of 400 to 100,000, preferably 500 to 50,000. The homopolymers have an especially preferred molecular weight of 500 to 50,000. Molecular weight is measured by gel permeation chromotography. The copolymers suitable herein are random non-cross-linked polymers.

The polymers of the anticalculus agents of interest herein are selected from homopolymers of monounsaturated monocarboxylic and dicarboxylic acids of 3 to 5 carbon atoms and from copolymers of such an acid, anhydrides and salts thereof, with at least one principal conomer selected from acrylamides, alkyl acrylates, alkyl itaconates, vinyl sulfonic acid, hydroxyalkyl acrylates, alkoxyalkyl acrylates, lower alkenyl carboxylates, styrene sulfonic acids, allyloxyhydroxyalkane sulfonic acids, acrylamidoalkane sulfonic acids, sulfoloweralkyl acrylates, polymerized vinyl alcohols, anhydrides thereof, salts thereof, and mixtures thereof.

As used herein, the generic term "acrylates" also includes "methacrylates".

The copolymers referred to above are copolymers of a carboxylic monomer selected from carboxylic acid, salts and anhydrides thereof, and at least one principal copolymerizable monomer. The copolymers can also include up to about 30%, preferably up to 20% and especially 2 to 10%, of at least one secondary copolymerizable monomer as long as such secondary comonomer does not substantially deleteriously affect performance of the copolymers defined above as anticalculus agents.

The anticalculus copolymers contain at least 30% by weight of the carboxylic monomer, in acid or anhydride or salt form, preferably 40 to 99%. The principal comonomer is used at the level of up to about 70%, preferably 1 to 60%. The principal comonomer and the carboxylic monomer form the copolymer unless the secondary monomer is used. The secondary comononer, if used, is used in place of a portion of the principal comonomer.

Suitable carboxylic monomers are selected from monounsaturated carboxylic acids of 3 to 5 carbons, anhydrides and salts thereof, which have at least one activated olefinic double bond and at least one carboxyl group. Monocarboxylic and dicarboxylic acids are preferred.

Illustrative of such acids are acrylic, methacrylic, ethacrylic, alpha-chloroacrylic, crotonic, beta-acryloxy propionic, sorbic, alpha-chlorosorbic, cinnamic, beta-styrylacrylic, muconic, itaconic, citraconic, mesaconic, glutaconic, aconitic, alpha-phenylacrylic, 2-benzyl acrylic, 2-cyclohexyacrylic, angelic, umbellic, fumaric, maleic acid and anhydrides thereof. The preferred carboxylic acids are selected from acrylic acid, methacrylic acid, itaconic acid, maleic acid and its anhydride, citraconic acid, and mesaconic acid, especially acrylic acid, methacrylic acid, itaconic acid maleic acid and maleic anhydride. The acrylic, methacrylic and maleic acids are especially preferred.

As already noted, the principal comonomers are selected from acrylamides, alkyl acrylates, alkyl itaconates, vinyl sulfonic acids, hydroxyalkyl acrylates, alkoxyalkyl acrylates, lower alkenyl carboxylates, styrene sulfonic acids, allyloxyhydroxyalkane sulfonic acids, acrylamidoalkane sulfonic acids, sulfoloweralkyl acrylates, polymerized vinyl alcohols, and anhydrides and salts thereof.

Suitable acrylamides as principal comonomers are defined as follows:

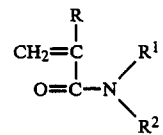

where R is hydrogen or methyl and $R^1$ and $R^2$ are individually selected from hydrogen, alkyl and substituted alkyl groups each containing a total of 1 to 12, preferably 1 to 8 carbons. Preferred acrylamides are the substituted acrylamides where either $R^1$ or $R^2$ is not hydrogen. Substituents on the alkyl groups include alkyl, aryl, hydroxyl, hydroxyalkyl, carboxylic acid, and keto groups. Specific examples of substituted acrylamides include t-butyl acrylamide, isopropyl acrylamide, isobutyl acrylamide, methyl acrylamide, t-butyl methacrylamide, 2-(2,4,4-trimethyl pentyl) acrylamide, 2-(2-methyl-4-oxopentyl) acrylamide, hydroxymethyl acrylamide, hydroxypropyl acrylamide, diacetone acrylamide, and 3-acrylamido-3-methyl butanoic acid.

The alkyl acrylates as principal comonomers are defined as follows:

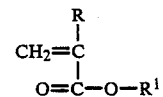

where R is hydrogen or methyl and $R^1$ is selected from alkyl groups of 1 to 6 carbons and substituted alkyl groups where $R^1$ is defined as $R^2-Y$, where $R^2$ is an alkyl group containing from 1 to 6 carbon atoms and Y is $-SO_3X$, $-C(O)R^3$, or $-CO_2X$ where X is hydrogen, alkali metal, alkaline earth metal, or ammonium, and $R^3$ is alkyl of 1 to 3 carbon atoms. In a preferred embodiment, the $R^1$ group is unsubstituted of 1 to 4 carbon atoms. Specific example of suitable monomeric alkyl acrylates and methacrylates include ethyl acrylate, ethyl methacrylate, sulfoproyl acrylate, and carboxyethyl acrylate.

The alkyl itaconates as principal comonomers have the following structure:

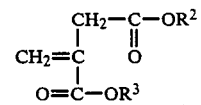

where $R^2$ and $R^3$ are individually selected from hydrogen, alkyl and substituted alkyl groups of 1 to 12 carbon atoms in the alkyl group, provided that both $R^2$ and $R^3$ are not hydrogen although either $R^2$ or $R^3$ can be hydrogen. Substituents on the $R^2$ and $R^3$ groups include lower alkyl, aryl such as phenyl, and keto groups, however, in a preferred embodiment, $R^2$ and $R^3$ are individually selected from unsubstituted lower alkyl groups of 1 to 4 carbon atoms. Specific examples of preferred $R^2$ and $R^3$ groups include methyl, ethyl, propyl, isopropyl, butyl and isomeric forms thereof, and the like. Preferred herein are the diesters of itaconic acid. Specific examples of preferred itaconic acid esters include dimethyl itaconate, diethyl itaconate and dibutyl itaconate.

Vinyl sulfonic acid and salts thereof of the principal comonomers are defined as follows:

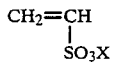

where X is selected from hydrogen, alkali metal, alkaline earth metal, and an ammonium groups, preferably an alkali metal and ammonium groups. Preferred vinyl sulfonic acid salt is sodium vinyl sulfonate where X in the above formula is sodium.

Hydroxyalkyl acrylates of the principal comonomers are defined as follows:

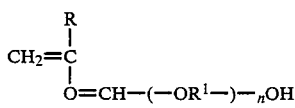

where R is hydrogen or a lower alkyl of 1 to 3 carbon atoms, preferably hydrogen or methyl; $R^1$ is selected from lower alkylene groups of 2 to 4, preferably 2 to 3 carbon atoms; and n is an integer from 1 to 5. Some specific examples of suitable hydroxyalkyl acrylates include hydroxypropyl acrylate and hydroxypropyl methacrylate.

The alkoxyalkyl acrylates of the principal comonomers are defined as follows:

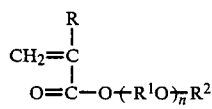

where R is hydrogen or methyl, $R^1$ is an alkylene group containing from 2 to 4, but preferably 2 to 3 carbon atoms, n is an integer from 1 to 5 but preferably 1 to 3, and $R^2$ is an alkyl group containing from 1 to 10 preferably 1 to 4 carbon atoms. Specific examples of alkoxyalkyl acrylate monomers include methoxyethyl acrylate, cellosolve methacrylate, and 2-(2-ethoxyethoxy) ethyl acrylate.

The vinyl carboxylate monomers are defined as follows:

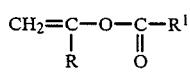

where R is hydrogen or a lower alkyl group of 1 to 6 carbon atoms, preferably hydrogen or alkyl of 1 to 2, and $R^1$ is selected from alkyl groups of 1 to 12 carbon atoms, preferably 1 to 8. The vinyl carobxylates, in polymerized form, can be hydrolyzed to contain polymerized vinyl alcohol which has repeating units of the following structure:

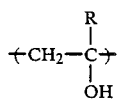

where R is hydrogen or a lower alkyl group of 1 to 6 carbon atoms, preferably hydrogen or alkyl of 1 to 2. The R group of the hydrolyzed carboxylates corresponds to the R group on the vinyl carboxylates. Specific examples of vinyl carboxylates include vinyl acetate, vinyl propionate, and 2-propenyl acetate.

Styrene sulfonic acids and salts thereof of the principal comonomers are defined as follows:

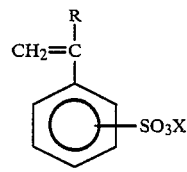

where R is hydrogen or a lower alkyl group of 1 to 6 carbon atoms, but preferably hydrogen, and X is hydrogen, alkali metal or alkaline earth metal or ammonium but particularly hydrogen, ammonium or alkali metal. A particularly suitable sulfonic acid is styrene sulfonic acid where R is hydrogen and the $-SO_3$ group is at the 3 or 4 position on the phenyl ring. The salts of styrene sulfonic acids are water-soluble. The sodium salt of styrene sulfonic acid is available commercially.

The allyloxyhydroxyalkane sulfonic acids and salts thereof of the principal comonomers are defined as follows:

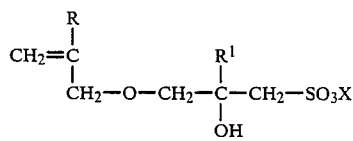

where R and $R^1$ are each hydrogen or methyl, and X is selected from hydrogen, alkali metal, alkaline earth metal and ammonium groups. Preferred monomer in this group is the sodium salt of 3-allyloxy-2-hydroxypropanesulfonic acid.

Suitable acrylamidoalkane sulfonic acids and salts thereof of the principal comonomers have the general formula

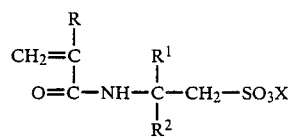

where R is hydrogen or methyl; X is selected from hydrogen, ammonium, alkali metals or alkaline earth metals, particularly hydrogen, ammonium, or an alkali metal; and $R^1$ and $R^2$ are individually selected from hydrogen and alkyl groups of 1 to 4 carbon atoms. In a preferred embodiment, R is hydrogen and $R^1$ and $R^2$ are each an alkyl group of 1 of 3 carbon atoms. The letter X in the above structural formula represents hydrogen or any metal cation which does not adversely affect the water solubility of the polymer, such as sodium, potassium and ammonium cations. In addition, X may also represent calcium, magnesium, and lithium, since they do not present any adverse effects on the solubility of the polymer. The acrylamidoalkane sulfonic acid monomer which has been found to be particularly suitable in accordance with the present invention is 2-acrylamido-2-methylpropane sulfonic acid which has the following structural formula:

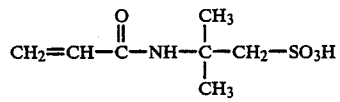

Sulfoalkyl acrylates of the principal comonomers have the following structure:

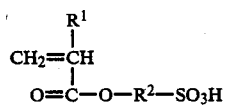

where $R^1$ is selected from hydrogen, methyl and the group

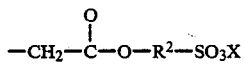

where $R^2$ is selected from alkylene groups of 1 to 12 carbons, preferably 2 to 4 carbons; and where X is selected from hydrogen, alkali metals, alkaline earth metals, and ammonium but particularly hydrogen, sodium, potassium, calcium, magnesium, and ammonium. The sulfo group $-SO_3X$, is preferably located on the last carbon atom of the $R^2$ group. The $R^2$ group can be substituted or unsubstituted. Substituents on the $R^2$ group are selected from those substituents which do not adversely affect the anticalculus activity of the copolymer. Preferred sulfoalkyl acrylates include 2-sulfoethyl methacrylate, 3-sulfopropyl acrylate, 3- sulfopropyl methacrylate, bis-(3-sulfopropyl) itaconate.

The monomers can be prepared, if desired, in a conventional manner but they are commercially available and, therefore, can be purchased. Polymerization of the monomers results in an essentially non-crosslinked random copolymer, the molecular weight of which can be adjusted with a little trial and error. The copolymer is preferably formed in a high yield ranging from about 50% to about 99% by weight of the comonomers.

It is also a requirement that the copolymer agent be soluble in water. Thus, high solubility of the agents is not essential but desirable. The polymer of the anticalculus agent can be shipped in drums as a concentrated aqueous solution containing in the range of about 20% to about 50% by weight of solids per 100 parts of solution, which requires solubility to the extent of at least 20 weight parts per 100 parts of water.

Polymerization of the monomers identified herein can be carried out in a mutual solvent for both, such as in a lower alkanol of about 1 to 6 carbon atoms, or in water, with an effective amount of a free radical initiator sufficient to produce the desired composition within an acceptable period of time. The monomeric acids can be used as such or they can be in a partially or a completely neutralized form prior to polymerization.

The reaction is conveniently carried out in water as the only reaction medium at a temperature in the range of about 30° to about 130° C. usually at atmospheric or slightly elevated pressure. The concentration of the copolymer formed may range from about 5% to about 50% by weight, based on total solids, which solution can be shipped directly.

The acid numbers of the copolymers formed, as determined by a conventional titration with KOH, may range from about 230 to about 740, corresponding to a weight fraction of from 30% to about 95% by weight of monomer units having COOH groups. The preferred polymers have more than 50% by weight of free carboxyl groups and an acid number in the range of about 390 to about 700.

The sources of fluoride ions, or fluorine-providing compounds, required according to this invention as an essential component of the described composition, are well known in the art as anti-caries agents and also act as such agents in the practice of this invention. These compounds may be slightly soluble in water or may be fully water-soluble. They are characterized by their ability to release fluoride ions in water and by freedom from undesired reaction with other compounds of the oral preparation. Among these materials are inorganic fluoride salts, such as soluble alkali metal and alkaline earth metal salts, for example, sodium fluoride, potassium fluoride, ammonium fluoride, calcium fluoride, copper fluorides such as cuprous fluoride, zinc fluoride, barium fluoride, sodium fluorosilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluoride, sodium monofluorophosphate, and mixtures thereof, are preferred.

The amount of fluorine-providing compound is dependent to some extent upon the type of compound, its solubility, and the type of oral composition, but it must be a nontoxic amount, generally about 0.005 to about 3.0% in the composition. In a dentifrice composition, e.g. gel, cream, toothpaste or tooth powder, an amount of such compound which releases 50 to 3500 ppm of flourine ion by weight of the composition is considered satisfactory. Any suitable minimum amount of such compound may be used but it is preferable to employ sufficient compound to release about 300 to about 2,000 ppm, more preferably about 800 to about 1,500 ppm of fluoride ion. Typically, in the case of alkali metal fluorides and stannous fluoride, this component is present in an amount up to about 2% by weight, based on the weight of the composition, and preferably in the range of about 0.05% to 1%. In the case of sodium monofluorophosphate, the compound may be present in an amount of about 0.1-3%, more typically about 0.2-1%.

In oral compositions such as mouthwashes, lozenges and chewing gum, the fluorine-providing compound is typically present in an amount sufficient to release up to about 500 ppm, preferably about 25 to about 300 ppm by weight of fluoride ion. Generally, about 0.005 to about 1.0 weight percent of such compound is present.

Water employed in the preparation of commercially suitable oral compositions should preferably be of low ion content and free of organic impurities. Water comprises from about 2% to about 5%, preferably from about 20% to about 95% of the compositions of this invention. When in the form of toothpastes, the amount of water is preferably from about 2% to about 45%, while mouthwashes preferably contain from about 45% to about 95%.

In a toothpaste, the liquid vehicle may comprise water and humectant typically in an amount ranging from about 10% to about 90% by weight of the preparation. Glycerine, propylene glycol, sorbitol, polypropylene glycol and/or polyethylene glycol exemplify suitable humectants or carriers. Also advantageous are liquid mixtures of water, glycerine and sorbitol. In clear gels, where the refractive index is an important consideration, about 3–30% by weight of water, 0 to about 80% by weight of glycerine, and about 20–80% by weight of sorbitol, is preferably employed.

In certain desirable forms of this invention, the oral compositions may be substantially solid or pasty in character, such as tooth powder, a dental tablet, toothpaste, gel or dental cream. The vehicle of such solid or pasty oral preparations generally contains a polishing material. Examples of polishing materials are water-insoluble sodium metaphosphate, potassium metaphosphate, tricalcium phosphate, dehydrated calcium phosphate, anhydrous dicalcium phosphate, calcium pyrophosphate, magnesium orthophosphate, trimagnesium phosphate, calcium carbonate, aluminum silicate, zirconium silicate, silica, bentonite, and mixtures thereof. Other suitable polishing materials include the particulate thermosetting resins described in U.S. Pat. No. 3,070,510 such as formaldehydes of melamine, phenol, and urea, and cross-linked polyepoxides and polyesters. Preferred polishing materials include crystalline silica having particle size of up to about 5 microns, a mean particle size of up to about 1.1 microns, and a surface area of up to about 50,000 cm$^2$/gm, silica gel or colloidal silica, and complex amorphous alkali metal alumino-silicate.

When visually clear gels are employed, a polishing agent of colloidal silica and alkali metal alumino-silicate complexes are particularly useful since they have refractive indices close to the refractive indices of the liquid gelling agent.

The linear, molecularly dehydrated polyphosphate salts operative herein as abrasive dental additives are well known, being generally employed in the form of their wholly or partially neutralized water soluble alkali metal or ammonium salts and mixtures thereof. Representative examples include sodium hexametaphosphate, sodium tripolyphosphate, disodium diacid, trisodium monoacid, and tetrasodium pyrophosphates, and the like. Linear polyphosphates correspond to $(NaPO_3)_n$ where n is about 2 to about 125. They are generally employed in the instant oral compositions in approximate weight amounts of 0.1 to 7%, preferably 1 to 5%.

The polishing material or dental abrasive is generally present in the solid or pasty compositions in weight concentrations of about 10% to about 99%. Preferably, it is present in amounts ranging from about 10% to about 75% in toothpaste, and from about 0% to about 99% in tooth powder.

Toothpastes, creams and gels typically contain a natural or synthetic thickener or gelling agent in proportions of about 0.1 to about 10, preferably about 0.5 to about 5, weight percent. A suitable thickener is synthetic hectorite, a synthetic colloidal magnesium, alkali metal silicate complex clay, and carboxyvinyl polymer or polyacrylic acid of intermediate molecular weight.

The oral compositions of this invention can contain a variety of optional conventional oral ingredients. Such optional ingredients include sudsing agents, flavoring agents, sweetening agents, binding agents, coloring agents, humectants, and pigments.

A preferred optional ingredient is a sudsing agent. Suitable sudsing agents are those which are reasonably stable and form suds throughout a wide pH range, i.e., non-soap anionic, cationic, zwitterionic and amphoteric organic synthetic detergents. Sudsing agents of these types are described more fully in Agricola et al U.S. Pat. No. 3,959,458 and in Haefele U.S. Pat. No. 3,937,807.

Flavoring agents can also be added to the instant compositions. Suitable flavoring agents include oil of wintergreen, oil of peppermint, oil of spearmint, oil of sassafras, and oil of clove. Sweetening agents which can be used include saccharin, dextrose, levulose, aspartame, D-tryptophan, dihydrochalcones, acesulfame and sodium cyclamate. Flavoring agents are generally used in the compositions at levels of from about 0.4% to about 2% by weight and sweetening agents at levels of from about 0.1% to about 5% by weight.

Binders can also be used with the toothpastes of the present inventions. Such binders include, for example, xanthan gum, carrageenan (Irish moss), and carboxyvinyl polymers or polyacrylic acids of intermediate molecular weight. These binders are generally present at a level of from about 0.1% to 1%.

Another optional component of the compositions herein is a humectant. The humectant serves to keep the toothpaste compositions from hardening upon exposure to air and in mouthwashes, give a moist feel to the mouth. Certain humectants can also impart desirable sweetness or flavor to mouthwash and toothpaste compositions. The humectant, on a pure humectant basis, generally comprises from about 0% to 70%, preferably from about 5% to 55%, by weight of the compositions herein.

Suitable humectants for use in this invention include edible polyhydric alcohols such as glycerine, sorbitol, xylitol and propylene glycol. Sorbitol is frequently employed as a 70% aqueous solution.

The mouthwashes herein may also contain ethanol in an amount of from about 0 to about 30%, preferably 5 to 25%, as a germicide.

The pH of the compositions herein is in the range of 6 to 10, preferably from 7 to 9. The pH is preferably achieved through a proper balancing of the pyrophosphate salts or by the addition of an alkaline or acidic agent.

The compositions herein are made using conventional mixing techniques.

In certain forms of the invention, the oral composition may be substantially liquid in character, such as mouthwash or rinse. In such a composition, the vehicle is typically a water-alcohol mixture which desirably includes a humectant. Generally, the weight ratio of water to alcohol is the range of from about 1:1 to about 20:1, preferably about 3:1 to 10:1 and more preferably about 4:1 to about 6:1. The total amount of water-alcohol mixture in this type of preparation is typically in the range of from about 70% to about 99.9% by weight of the preparation.

The following examples further describe and demonstrate preferred embodiments within the scope of the present invention. The examples are given solely for the purpose of illustration and are not to be construed as limitations of this invention. Many variations thereof are possible without departing from the invention's spirit and scope.

EXAMPLE I

Calcium phosphate precipitation was studied pursuant to the pH-stat technique described in Ex. 1 of U.S. Pat. No. 4,627,977. The rate of formation of hydroxyapatite (HAP) was followed titrimetrically by the consumption of sodium hydroxide using the pH-stat instrument of Brinkman Instruments Type 600 series.

Solutions of calcium chloride, sodium phosphate, and other components were mixed and stirred at a constant temperature of 37° C., and the amount of sodium hydroxide required to keep the pH constant at 7.40 was then continuously recorded as a function of time. Nitrogen gas presaturated with H$_2$O at 37° C. was bubbled through the solution to exclude carbon dioxide. In this system, it is believed that the precipitation and crystal growth occur in two distinct stages. The first stage, which corresponds to the initial rise in consumption of sodium hydroxide, represents the formation of amorphous calcium phosphate, which is less basic than hydroxyapatite, whereas the second stage, which corresponds to the second rise in consumption of sodium hydroxide, represents the crystal growth of hydroxyapatite (HAP).

Table A, below, sets forth results of the tests wherein pH was 7.40, temperature 37° C., calcium ion and phosphate ion concentrations were each $3.2 \times 10^{-3}$M, and the composition of the phosphorus-containing compound and the polymer of the anticalculus agents is given on weight basis:

TABLE A

| Exp. No. | Polymer | Polymer Dosage (ppm) | Phosphorus containing compound (ppm) | | | | | Time of HAP inhibition (min) | | |
|---|---|---|---|---|---|---|---|---|---|---|
| | | | A | B | C | D | E | Actual | Expected | Synergism |
| 1. | None | 0 | — | — | — | — | — | 3 | — | NA |
| 2. | AA:MAA:t-BuAm (60/20/20) | 30 | — | — | — | — | — | 4 | — | NA |
| 3. | AA:MAA:t-BuAm (60/20/20) | 0 | 10 | — | — | — | — | 7 | — | NA |
| 4. | AA:MA:t-BuAm (60/20/20) | 30 | 10 | — | — | — | — | 25 | 11 | 14 |
| 5. | AA:MA:t-BuAm (60/20/20) | 0 | — | 10 | — | — | — | 12 | — | NA |
| 6. | AA:MA:t-BuAm (60/20/20) | 30 | — | 10 | — | — | — | 140 | 16 | 124 |
| 7. | AA:MA:t-BuAm (60/20/20) | 0 | — | — | 10 | — | — | 17 | — | NA |
| 8. | AA:MA:t-BuAm (60/20/20) | 30 | — | — | 10 | — | — | 180 | 21 | 159 |
| 9. | AA:MA:t-BuAm (60/20/20) | 0 | — | — | — | 10 | — | 7 | — | NA |
| 10. | AA:MA:t-BuAm (60/20/20) | 30 | — | — | — | 10 | — | 27 | 11 | 16 |
| 11. | AA:MA:t-BuAm (60/20/20) | 0 | — | — | — | — | 10 | 13 | — | NA |
| 12. | AA:MA:t-BuAm (60/20/20) | 30 | — | — | — | — | 10 | 68 | 17 | 51 |
| 13. | AA:AMPS (51:49) | 30 | — | — | — | — | — | 4 | — | NA |
| 14. | AA:AMPS (51:49) | 30 | — | — | — | — | 10 | 63 | 17 | 46 |
| 15. | PMA | 30 | — | — | — | — | — | 27 | — | NA |
| 16. | PMA | 30 | — | — | — | — | 10 | 235 | 40 | 195 |
| 17. | AA:SEM (80:20) | 30 | — | — | — | — | — | 5 | — | NA |
| 18. | AA:SEM (80:20) | 30 | — | — | — | — | 10 | 53 | 18 | 35 |
| 19. | AA:DMI (80:20) | 30 | — | — | — | — | — | 4 | — | NA |
| 20. | AA:DMI (80:20) | 30 | — | — | — | — | 10 | 47 | 17 | 30 |
| 21. | AA:HPA (63:37) | 30 | — | — | — | — | — | 5 | — | NA |
| 22. | AA:HPA (63:37) | 30 | — | — | — | — | 10 | 57 | 18 | 39 |
| 23. | AA:VOH:AMPS (50:20:30) | 30 | — | — | — | — | — | 4 | — | NA |
| 24. | AA:VOH:AMPS (50:20:30) | 30 | — | — | — | — | 10 | 45 | 17 | 24 |
| 25. | AA:SSS:AMPS (60:20:20) | 30 | — | — | — | — | — | 4 | — | NA |
| 26. | AA:SSS:AMPS (60:20:20) | 30 | — | — | — | — | 10 | 95 | 17 | 78 |
| 27. | AA:MAA:t-BuAm (60:20:20) | 40 | — | — | — | — | — | 7 | — | NA |
| 28. | AA:MAA:t-BuAm (60:20:20) | 40 | — | — | — | — | 10 | 120 | 20 | 100 |
| 29. | AA:MAA:t-BuAm (60:20:20) | 25 | — | — | — | — | — | 4 | — | NA |
| 30. | AA:MAA:t-BuAm (60:20:20) | 25 | — | — | — | — | 15 | 118 | 68 | 50 |
| 31. | AA:MAA:t-BuAm (60:20:20) | 0 | — | — | — | — | 15 | 32 | — | NA |
| 32. | PAA | 30 | — | — | — | — | — | 3 | — | NA |
| 33. | PAA | 30 | — | — | — | — | 10 | 35 | 16 | 19 |
| 34. | AA:t-BuAm:AMPS | 30 | — | — | — | — | — | 5 | — | NA |
| 35. | AA:t-BuAm:AMPS | 30 | — | — | — | — | 10 | 55 | 18 | 37 |

In Table A, the following contractions appear:

| In TABLE A, the following contractions appear: | | |
|---|---|---|
| AA | = | acrylic acid |
| t-BuAm | = | tertiary butyl acrylamide |
| MAA | = | methacrylic acid |
| HPA | = | hydroxypropyl acrylate |
| AMPS | = | 2-acrylamido -2-methylpropane sulfonic acid |
| DMI | = | dimethyl itaconate |
| SSS | = | sodium styrene sulfonate |
| SEM | = | 2-sulfoethyl methacrylate |
| PMA | = | polymaleic acid |
| PAA | = | polyacrylic acid |
| VOH | = | vinyl alcohol |

The "Actual" time given in Table A, was the actual time observed experimentally; the "Expected" time was obtained by adding the known inhibition values of both components of the anticalculus agents; and synergism is indicated by subtracting the "Expected" time from the "Actual" time where values are positive. The notation "NA" in Table A, represents "Not Available" and indicates a situation where synergism does not apply.

The polymers used and noted in Table A, above, are further defined as follows:

AA:MAA:t-BuAm (60:20:20) copolymer of acrylic acid, methacrylic acid, and tertiary butyl acrylamide with molecular weight of about 10,000.

AA:AMPS (51:49) copolymer of acrylic acid and 2-acrylamido-2-methylpropane sulfonic acid with molecular weight of about 10,000.

PMA was a homopolymaleic acid with molecular weight of about 500.

AA:SEM (80:20) copolymer of acrylic acid and 2-sulfoethyl methacrylate with molecular weight of about 10,000.

AA:DMI (80:20) copolymer of acrylic acid and diemthyl itaconate with molecular weight of about 10,000.

AA:HPA (63:37) copolymer of acrylic acid and hydroxypropyl acrylate with molecular weight of about 7,000.

AA:VOH:AMPS (50:20:30) copolymer of acrylic acid, vinyl alcohol, and 2-acrylamido-2-methylpropane sulfonic acid with molecular weight of about 10,000.

AA:SSS:AMPS (60:10:30) copolymer of acrylic acid, sodium styrene sulfonic acid, and 2-acrylamido-2-methylpropane sulfonic acid with molecular weight of about 10,000.

PAA is a homopolyacrylic acid with molecular weight of about 7,000.

The data in Table A demonstrates that mixtures of a phosphorus-compound and a polymer exhibit synergistic results in terms of hydroxyapatite (HAP) inhibition. All of the combinations exhibited synergistic HAP inhibition, however, certain combinations of the phosphorus-containing compounds and polymers showed superior synergistic results. Polymers which showed superior synergism included copolymer of acrylic acid, methacrylic acid, and tertiary butyl acrylamide; copolymer of acrylic acid and 2-acrylamido-methylpropane sulfonic acid; and homopolymer of maleic acid. The tested phosphorus-containing compounds which gave superior results included aminotri(methylene phosphonic acid); hydroxyethane-1,1-diphosphonic acid; and 2-phosphonobutane-1,2,4-tricarboxylic acid.

Time of crystal growth inhibition of about 10 minutes is acceptable but in preferred embodiments, the time is in excess of about one half hour. Of course, this time period can be increased by increasing amount of the anticalculus agent.

EXAMPLE 2

This example demonstrates the use of mixtures of two polymers and a phosphorus-containing compound.

The polymers employed herein included a 60:20:20 copolymer of acrylic acid (AA), methacrylic acid (MAA), and tertiary butyl acrylamide (t-BuAm) with molecular weight of about 10,000 and a homopolymer of acrylic acid (PAA) with molecular weight of about 5,100. The phosphorus-containing compound was 2-phosphonobutane-1,2,4-tricarboxylic acid (PCA). Amount of each polymer used was 30 ppm and amount of the Phosphorus-containing compound was 10 ppm. Results of the hydroxyapatite (HAP) inhibition is given in Table B, below:

TABLE B

| Exp. No. | Polymer 1 | Polymer 2 | Phos. Cont. Compound | Time of HAP Inhibition (min.) | | |
|---|---|---|---|---|---|---|
| | | | | Actual | Expected | Synergism |
| 36 | AA:MAA:t-BuAm | — | — | 4 | — | NA |
| 37 | — | — | 3 | — | NA | |
| 38 | — | — | PCA | 13 | — | NA |
| 39 | AA:MAA:t-BuAm | PAA | PCA | 615 | 20 | 595 |
| 40 | AA:MAA:t-BuAm | PAA | — | | | |
| 41 | AA:MAA:t-BuAm | — | PCA | 68 | 17 | 51 |
| 42 | — | PAA | PCA | 35 | 16 | 19 |

Results in Table B indicate the incredible inhibition of hydroxyapatite of 615 minutes with an antiscalant agent containing three components: a copolymer of acrylic acid, methacrylic acid, and t-butyl acrylamide; a homopolymer of acrylic acid; and a phosphonobutane tricarboxylic acid.

It is believed that the polymers disclosed herein would also be effective in inhibiting hydrolysis of the phosphorus-containing compounds, particularly polyphosphates, in the presence of saliva or in the presence of pyrophosphatase enzyme.

What is claimed is:

1. An oral composition comprising:
   (a) an effective amount of a fluoride source,
   (b) effective amount of a dental abrasive; and
   (c) 0.01 to 10% by weight of an anticalculus agent selected from at least one phosphorus-containing compound and at least one polymer in the weight ratio of 1:10 to 10:1; said compound is selected from the group consisting essentially of amino phosphonic acids, diphosphonic acids, phosphonoalkane carboxylic acids, hydroxy phosphonocarboxylic acids, polyphosphoric acids, polyol phosphate esters, amino phosphonates, salts thereof, and mixtures thereof and whereas said polymer is selected from the group consisting essentially of homopolymers of a carboxylic monomer selected from the group consisting essentially of monounsaturated monocarboxylic and dicarboxylic acids of 3 to 5 carbon atoms, salts and anhydrides of such acids, and mixtures of such carboxylic monomers, and from copolymers containing at least 30% by weight of such carboxylic monomer and at least 5% by weight of a principal comonomer.

2. Composition of claim 1 wherein said copolymer is composed of at least one of said carboxylic monomers and at least one principal comonomer selected from the group consisting essentially of acrylamides, alkyl acrylates, alkyl itaconates, vinyl sulfonic acid, hydroxyalkyl acrylates, alkoxyalkyl acrylates, loweralkenyl carboxylates, vinyl alcohol, styrene sulfonic acids, allyloxyhydroxyalkane sulfonic acids, acrylamidoalkane sulfonic acids, sulfoalkyl acrylates, salts and anhydrides thereof, and mixtures of such comonomers.

3. Composition of claim 2 wherein amount of said fluoride source is 0.005 to 3.0% by weight of said oral composition, wherein amount of said carboxylic monomer is 40 to 90% in said copolymers, and wherein molecular weight of said homopolymers and said copolymers is in the range of about 400 to 100,000.

4. Composition of claim 3 wherein said copolymer contains up to 60% of at least one of said principal comonomers; wherein amount of said fluoride source is 0.05 to 1%, and wherein amount of said anticalculus agent is 0.1 to 5%.

5. Composition of claim 4 wherein said carboxylic monomer is selected from acrylic acid, methacrylic acid, itaconic acid, maleic acid and its anhydride, citraconic acid, mesaconic acid, salts of such acids, and mixtures thereof; where acrylamides are defined as follows:

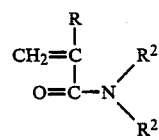

where R is selected from hydrogen and methyl groups; and $R^1$ and $R^2$ are individually selected from hydrogen and alkyl groups of 1 to 12 carbon atoms; where alkyl acrylates are defined as follows:

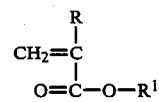

where R is selected from hydrogen and methyl groups and $R^1$ is selected from alkyl groups of 1 to 6 carbons and substituted alkyl groups where R' is defined as $R^2$ is an alkyl group of 1 to 6 carbons and Y is selected from $SO_3X$, $-COR^3$, and $-CO_2X$ where Y is selected from hydrogen, alkali metals alkaline earth metals, and ammonium groups and $R^3$ is selected from alkyl groups of 1 to 3 carbons; where alkyl itaconates are defined as follows:

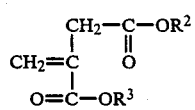

where $R^2$ and $R^3$ are individually selected from hydrogen and alkyl groups of 1 to 4 carbon atoms provided that both $R^2$ and $R^3$ are not hydrogens although either $R^2$ or $R^3$ can be hydrogen; where vinyl sulfonic acid and salts thereof are defined as follows:

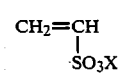

where X is selected from hydrogen, alkali metals, alkaline earth metals, and ammonium radicals; where hydroxyalkyl acrylates are defined as follows:

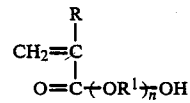

where R is selected from hydrogen and alkyl group of 1 to 3 carbons, $R^1$ is selected from alkylene groups of 2 to 4 carbons, and n is from 1 to 5; where alkoxyalkyl acrylates are defined as follows:

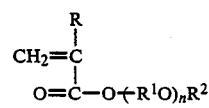

where R is selected from hydrogen and methyl groups, $R^1$ is selected from alkylene groups of 2 to 4 carbons, $R^2$ is selected from alkyl groups 1 to 10 carbons, and n is from 1 to 5; where loweralkenyl carboxylates are defined as follows:

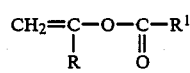

where R is hydrogen or a lower alkyl group of 1 to 6 carbon atoms, and $R^1$ is selected from alkyl groups of 1 to 12 carbon atoms; where vinyl alcohol is defined as follows:

where R is hydrogen or a lower alkyl group of 1 to 6 carbon atoms; where styrene sulfonic acids and salts thereof are defined as follows:

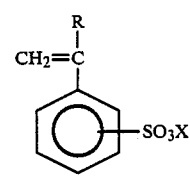

where R is selected from hydrogen and alkyl groups of 1 to 6 carbons, and X is selected from hydrogen, alkali metals, alkaline earth metals and ammonium radicals; where allyloxyhydroxyalkane sulfonic acids and salts thereof are defined as follows:

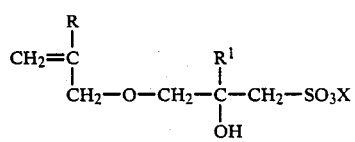

where R and $R^1$ are individually selected from hydrogen and methyl groups, and X is selected from hydrogen, alkali metals, alkaline earth metals, and ammonium radicals; where acrylamidoalkane sulfonic acids and salts thereof are defined as follows:

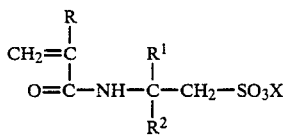

where R is selected from hydrogen and methyl groups, $R^1$ and $R^2$ are individually selected from hydrogen and alkyl groups of 1 to 4 carbons, X is selected from hydrogen, alkali metals, alkaline earth metals, and ammonium radicals; and where sulfoalkyl acrylates are defined as follows:

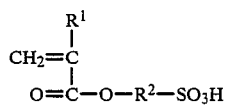

where $R^1$ is selected from hydrogen, methyl, and the group defined as

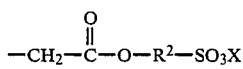

where $R^2$ is selected from alkylene groups of 1 to 12 carbon atoms and X is selected from hydrogen, alkali metals, alkaline earth metals, and ammonium radicals.

6. Composition of claim 5 where in said acrylamides, both $R^1$ or $R^2$ are not hydrogens; where in said alkyl acrylates, $R^1$ is selected from unsubstituted alkyl groups of 1 to 4 carbons; where in said alkyl itaconates $R^2$ and $R^3$ are individually selected from unsubstituted alkyl groups of 1 to 4 carbons; where in said sulfonic acid and salts thereof, X is selected from alkali metals and ammonium radicals; where in said hydroxyalkyl acrylates, R is selected from hydrogen and methyl groups and $R^1$ is selected from alkylene group of 2 to 3 carbons; where in said alkoxyalkyl acrylates, $R^1$ is selected from alkylene groups of 2 to 3 carbons, $R^2$ is selected from alkyl groups of 1 to 4 carbons, and n is from 1 to 3; where in said styrene sulfonic acids and salts thereof, R is hydrogen, X is selected from hydrogen, ammonium and alkali metal radicals, and said -SO₃X group is located at the 3 or 4 position on said phenyl ring; where in said acrylamidoalkane sulfonic acid and salts thereof, R is hydrogen and $R^1$ and $R^2$ are individually selected from alkyl groups of 1 to 3 carbons; and where in said sulfoalkyl acrylates, $R^2$ is selected from alkylene groups of 2 to 4 carbons and X is selected from hydrogen, sodium, potassium, calcium, magnesium, and ammonium radicals.

7. Composition of claim 6 wherein said phosphorus-containing compound is selected from amino phosphonic acids, diphosphonic acids, phosphomotricarboxylic acids, aminophosphonates, salts thereof, and mixtures thereof; wherein said amino phosphonic acids are defined as follows:

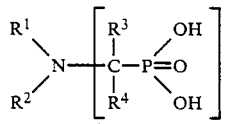

where $R^3$ and $R^4$ are individually selected from hydrogen and organic radicals, $R^1$ and $R^2$ are individually selected from hydrogen, organic radicals, and alkylene phosphonic radicals; said diphosphonic acids are defined as follows:

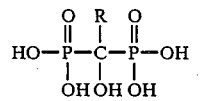

where R is selected from alkyl radicals of 1 to 5 carbon atoms; said phosphonotricarboxylic acids are defined as follows:

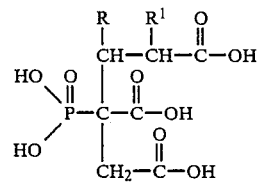

where R is selected from hydrogen, alkyl groups of 1 to 5 carbon atoms, and carboxy groups and $R^1$ is selected from hydrogen and methyl group; and said amino phosphonates are defined as follows:

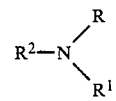

where R is

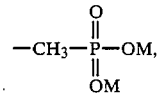

and $R^1$ is R or —CH₂—CH₂—OH and $R^2$ is R,

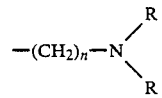

where M is hydrogen, ammonium, alkali metal or a combination thereof, and n is 1 to 6.

8. Composition of claim 7 having pH of 6 to 10 which is effective in inhibiting formation of dental calculus wherein amount of said fluoride source is sufficient to supply from about 50 ppm to about 2,500 ppm of fluoride ions; wherein amount of said anticalculus agent is 1 to 1000 ppm; wherein amount of said dental abrasive is 10 to 99%; wherein said composition also includes an oral vehicle; wherein said phosphorus-containing compound is selected from amino phosphonic acids, diphosphonic acids, phosphonoalkane carboxylic acids, and mixtures thereof; and wherein weight ratio of said Phosphorus-containing compound to said polymer is 1:5 to 5:1.

9. Composition of claim 8 wherein amount of said abrasive is 10 to 75% by weight selected from alkali metal hexammetaphosphate, alkali metal tripolyphosphate, dialkali metal diacid, trialkali metal monoacid, alkali metal tripolyphosphate, tetraalkali metal pyrophosphate, hydroxyethylethane diphosphonic acid, and mixtures thereof.

10. Composition of claim 7 wherein amount of said anticalculus agent is 0.1 to 5%, said copolymers of said anticalculus agent have molecular weight of 500 to 50,000 and said monounsaturated carboxylic acid is selected from acrylic acid, methacrylic acid, maleic acid or its anhydride, itaconic acid, and mixtures thereof.

11. Composition of claim 9 wherein said phosphorus-containing compound is selected from the group consisting essentially of aminotri(methylene phosphonic acid), hydroxyethan-1, 1-diphosphonic acid, 2-phosphonobutane-1,2,4-tricarboxylic acid, and mixtures thereof; and said polymer is selected from the following:
(a) 60:20:20 copolymer of AA:MAA t-BuAm
(b) 63:37 copolymer of AA:HPA
(c) 51:49 copolymer of AA:AMPS
(d) 100 homopolymer of maleic acid
(e) 100 homopolymer of acrylic acid
(f) 80:20 copolymer of AA:SEM
(g) 80:20 copolymer of AA:DMI
(h) 50:20:30 copolymer of AA:VOH:AMPS
(i) 60:20:20 copolymer of AA:SSS:AMPS
wherein the contractions used above are defined as follows:
AA = acrylic acid
MAA = methacrylic acid
SEM = 2-sulfoethyl methacrylate
HPA = hydroxypropyl acrylate
DMI = dimethyl itaconate
AMPS = 2-acrylamido-2-methylpropane sulfonic acid.
SSS = sodium styrene sulfonate 12. Composition of claim 11 wherein said polymers (a) to (i) have the following approximate molecular weights:
(a) 10,000
(b) 7,000
(c) 10,000
(d) 500
(e) 7,000
(f) 10,000
(g) 10,000
(h) 10,000
(i) 10,000

13. Composition of claim 11 wherein weight ratio of said phosphorus-containing compound to said polymer is 1:4 to 1:1.

14. Composition of claim 5 in toothpaste form wherein said fluoride source is selected from sodium fluoride, stannous fluoride, sodium monofluorophosphate, and mixtures thereof; amount of said dental abrasive is 10 to 75%; said dental abrasive is selected from silica, hydrated aluminum, insoluble metaphosphates, thermosetting polymerized resins, and mixtures thereof; and amount of said oral vehicle is 10 to 90% by weight.

15. Method of inhibiting dental calculus comprising applying to oral cavity composition as defined in claim 1.

16. Method comprising applying to teeth composition as defined by claim 5.

17. Method comprising applying to teeth composition as defined by claim 7.

18. Method comprising applying to teeth composition as defined by claim 14.

19. Composition of claim 6 wherein said phosphorus-containing compound is selected from amino phosphonic acids, diphosphonic acids, phosphonotricarboxylic acids, salts thereof, and mixtures thereof, said amino phosphonic acids are defined as follows:

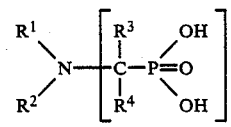

where $R^3$ and $R^4$ are individually selected from hydrogen and organic radicals, and where $R^1$ and $R^2$ are individually selected from hydrogen, organic radicals, and alkylene phosphonic radicals; said diphosphonic acids are defined as follows:

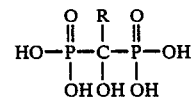

where R is selected from alkyl radicals of 1 to 5 carbon atoms; and said phosphonotricarboxylic acids are defined as follows:

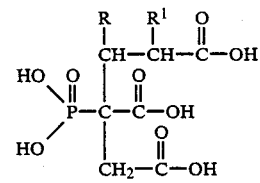

where R is selected from hydrogen, alkyl groups of 1 to 5 carbon atoms and carboxyl groups, and where $R^1$ is selected from hydrogen and methyl groups.

* * * * *